(12) United States Patent
Livak et al.

(10) Patent No.: US 6,964,848 B2
(45) Date of Patent: Nov. 15, 2005

(54) INVASION ASSAY

(75) Inventors: Kenneth J. Livak, San Jose, CA (US); Michael Y. Lucero, South San Francisco, CA (US); Muhammad A. Sharaf, Oakland, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/816,150

(22) Filed: Mar. 26, 2001

(65) Prior Publication Data

US 2003/0099941 A1 May 29, 2003

Related U.S. Application Data

(60) Provisional application No. 60/192,606, filed on Mar. 27, 2000.

(51) Int. Cl.$^7$ .......................... C12Q 1/68; C12P 19/34; C07H 21/02
(52) U.S. Cl. ..................... 435/6; 435/91.2; 536/23.1; 536/24.3
(58) Field of Search .................. 435/6, 91.2; 536/23.1, 536/24.3, 24.5; 702/19, 20

(56) References Cited

U.S. PATENT DOCUMENTS

| | | | |
|---|---|---|---|
| 5,843,669 A | 12/1998 | Kaiser et al. ................. | 435/6 |
| 5,846,717 A | 12/1998 | Brow et al. ................... | 435/6 |
| 5,874,283 A | 2/1999 | Harrington et al. ....... | 435/252.3 |
| 5,888,780 A | 3/1999 | Dahlberg et al. ......... | 435/91.53 |
| 5,985,557 A | 11/1999 | Prudent et al. ............. | 435/6 |
| 5,994,069 A | 11/1999 | Hall et al. .................. | 435/6 |
| 6,001,567 A | 12/1999 | Brow et al. ................. | 435/6 |
| 6,387,621 B1 * | 5/2002 | Wittwer ...................... | 435/6 |

FOREIGN PATENT DOCUMENTS

| | | |
|---|---|---|
| EP | 0 972 848 | 1/2000 |
| WO | WO 97/27214 | 1/1997 |
| WO | WO 98/23774 | 11/1997 |
| WO | WO 98/42873 | 3/1998 |
| WO | WO 01/32922 | 5/2001 |
| WO | WO 01/64958 | 9/2001 |
| WO | WO 01/90337 | 11/2001 |

OTHER PUBLICATIONS

Ryan et al., "Genotyping of Factor V Leiden in clinical samples using the Invader (TM)–Fret microtiter plate assay", American Journal of Pathology 153(5): 1649 (1998).

Fasman, 1989, *Practical Handbook of Biochemistry and Molecular Biology, UV Spectral Characteristics and Acidic Dissociation Constants of 280 Alkyl Bases, Nucleosides, and Nucleotides*, pp. 385–394, CRC Press, Boca Raton, FL.

Harrington, J.J., and Lieber, M.R., *J. Biol. Chem., DNA Structural Elements Required for FEN–1 Binding*, 270(9):4503–4508, 4506 (1995).

Kaiser, M.W. et al., *J. Biol. Chem., A Comparison of Eubacterial and Archaeal Structure–specific 5'–Exonucleases*, 274(30):21387–21394 (1999).

Kirk, R., *Introductory Statistics*, Wadsworth Publishing Co., Inc., Belmont, CA (1978).

Kornberg and Baker, 1992, *DNA Replication*, 2$^{nd}$ Ed., Freeman, San Francisco.

Lyamichev, V. et al., *Nature Biotech., Polymorphism identification and quantitative detection of genomic DNA by invasive cleavage of oligonucleotide probes*, 17:292–296 (1999).

Ryan, D. et al., *Molecular Diag., Non–PCR–Dependent Detection of the Factor V Leiden Mutation From Genomic DNA Using a Homogeneous Invader Microtiter Plate Assay*, 4(2):135–144 (1999).

Siegel, S., *Nonparametric Statistics*, McGraw–Hill, New York, p. 52, 1956.

* cited by examiner

Primary Examiner—Jeffrey Fredman
(74) Attorney, Agent, or Firm—Jones Day

(57) ABSTRACT

The invention relates to improved methods of detecting and characterizing polynucleotide sequences and variations in polynucleotide sequences. The invention further relates to a device that can be used to detect and characterize polynucleotide sequences and variations in polynucleotide sequences.

12 Claims, 8 Drawing Sheets

PRIMARY INVADER REACTION

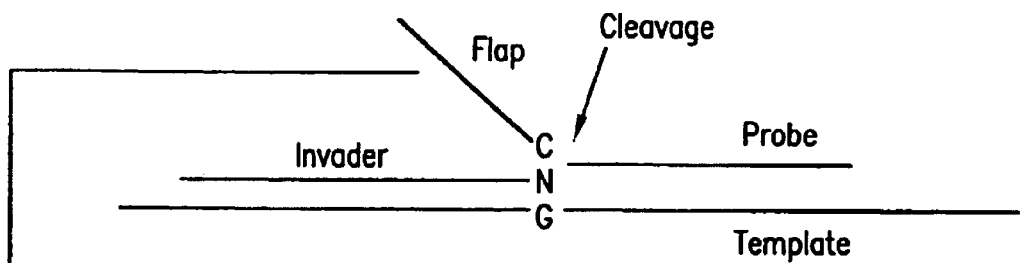

Cleavage because Invader disrupts duplex between Template and Probe

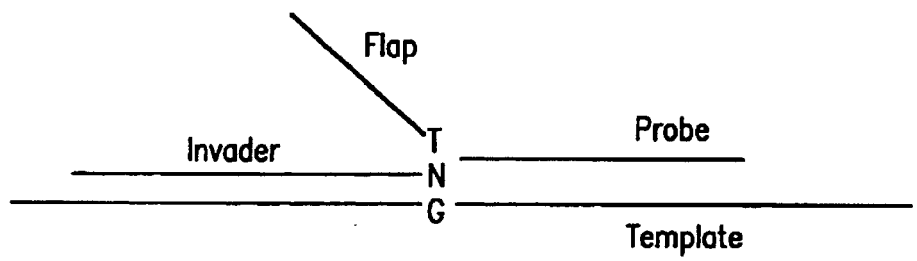

No cleavage because no disruption of base pairs between Template and Probe

SECONDARY INVADER REACTION

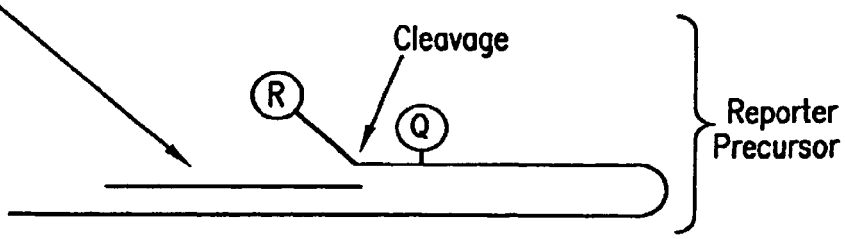

Flap from Primary Invader Reaction becomes Invader for Secondary Reaction. Cleavage liberates Reporter from Quencher, thus generating fluorescent signal.

FIG.2

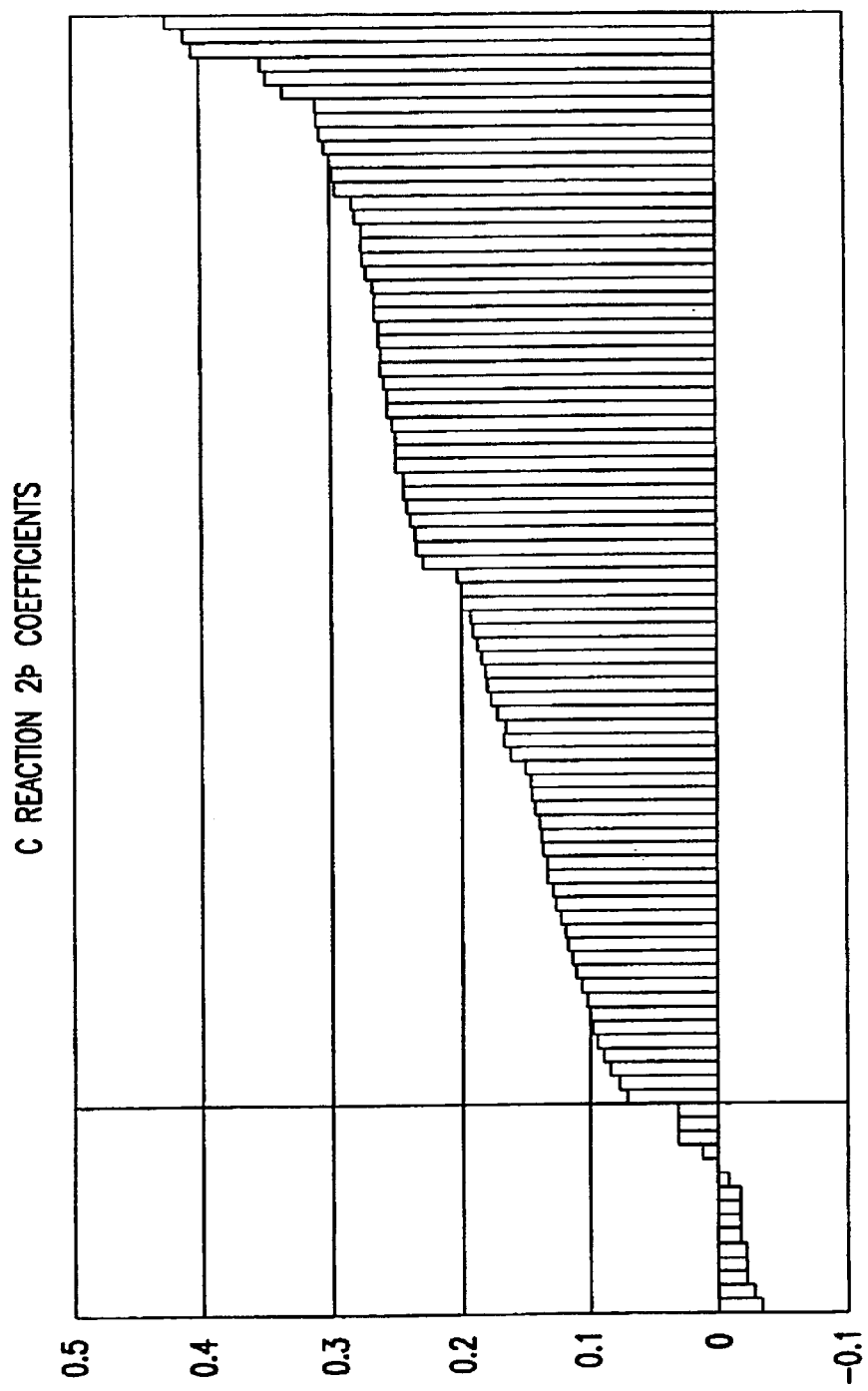

SEQUENCE LISTING

<160> NUMBER OF SEQ ID NOS: 7

<210> SEQ ID NO 1
<211> LENGTH: 26
<212> TYPE: DNA
<213> ORGANISM: Homo sapiens

<400> SEQUENCE: 1
attagaaagg aagggaagaa agcgaa                                    26

<210> SEQ ID NO 2
<211> LENGTH: 53
<212> TYPE: DNA
<213> ORGANISM: Homo sapiens

<400> SEQUENCE: 2
cgaactgccc ctttcggccg cttgcaccgc tctttccttc ccttctttcg ctt     53

<210> SEQ ID NO 3
<211> LENGTH: 30
<212> TYPE: DNA
<213> ORGANISM: Homo sapiens

<400> SEQUENCE: 3
gcttgacggg gaaagccggc gaacgtggcg                                30

<210> SEQ ID NO 4
<211> LENGTH: 30
<212> TYPE: DNA
<213> ORGANISM: Homo sapiens

<400> SEQUENCE: 4
cttgacgggg aaagccggcg aacgtggcga                                30

<210> SEQ ID NO 5
<211> LENGTH: 30
<212> TYPE: DNA
<213> ORGANISM: Homo sapiens

<400> SEQUENCE: 5
tgacggggaa agccggcgaa cgtggcgaga                                30

<210> SEQ ID NO 6
<211> LENGTH: 30
<212> TYPE: DNA
<213> ORGANISM: Homo sapiens

<400> SEQUENCE: 6
acggggaaag ccggcgaacg tggcgagaaa                                30

<210> SEQ ID NO 7
<211> LENGTH: 30
<212> TYPE: DNA
<213> ORGANISM: Homo sapiens

<400> SEQUENCE: 7
gggaaagccg gcgaacgtgg cgagaaagga                                30

INVASION ASSAY

This application claims the benefit of Provisional Application No. 60/192,606, filed Mar. 27, 2000.

FIELD OF THE INVENTION

The invention relates to improved methods of detecting and characterizing nucleic acid sequences and variations in nucleic acid sequences.

BACKGROUND OF THE INVENTION

Since the development of the Polymerase Chain Reaction (PCR), the demand for fast, reliable, and cost-effective tests for the detection of specific nucleic acid sequences has led to the development of a variety of new assay techniques. One of these, referred to as the INVADER™ (a trademark of Third Wave Technologies, Madison, Wis.) Assay, Invasion Cleavage Assay, or Invasion Assay, does not require the use of PCR. Invasion assays are highly sensitive and can be used to determine, for example, single-base differences of specific nucleotide targets. See, e.g., Lyamichev, V., et al., *Nature Biotech.* 17:292–296 (1999); and Ryan, D., et al., *Molecular Diag.* 4(2):135–144 (1999), each of which is incorporated herein by reference.

Invasion assays are based on the ability of some enzymes (e.g., endonucleases) to cleave nucleotide "flaps," such as those shown in FIG. 1A, that are formed when an oligonucleotide complementary to part of a DNA template overlaps with another oligonucleotide complementary to another part of the template. Specific enzymes, such as FEN 1, cleave flaps formed when the 3' end of an upstream oligonucleotide complementary to part of a DNA template overlaps with the 5' end of a downstream oligonucleotide complementary to another part of the DNA template. As shown in FIG. 1B, cleavage by such an enzyme of a downstream oligonucleotide (identified as Probe in FIG. 1B) provides a fragment that corresponds to the overlap between the two oligonucleotides complementary to the template. See Lyamichev, V., et al., *Nature Biotech.* 17:292–296 (1999).

Many endonucleases are thermostable, and can be used near the melt temperatures of the probe oligonucleotides they cleave. See Kaiser, M. W., et al., *J. Biol. Chem.* 274(30):21387–21394 (1999), and patents and published patent applications referred to herein. Most invasion assays take advantage of this characteristic by using a molar excess of a probe oligonucleotide that, at or near its melt temperature, will rapidly associate and disassociate with the template DNA. This allows a new, uncleaved probe to replace a cleaved probe such that when the experiment is complete, the quantity of cleaved fluorescent fragments is significantly larger than the amount of template DNA. See, Lyamichev, V., et al., *Nature Biotech.* 17:292–296 (1999).

FIG. 2 provides a representation of an invasion assay that is disclosed by, for example, U.S. Pat. No. 5,994,069, which is incorporated herein by reference. In this assay, the fragment cleaved from a probe oligonucleotide invades a second structure (referred to herein as a "reporter precursor") that contains fluorescent reporter R and a quencher Q. Association of the probe fragment with the second structure forms a flap that is cleaved by enzyme in the mixture. This cleavage breaks the connection between the reporter R and quencher Q and provides a fluorescent reporter fragment.

Theoretically, cleavage of the reporter precursor shown in FIG. 2 can occur only after a secondary invader oligonucleotide fragment is created by the primary invasion reaction. In some cases, however, the primary invader oligonucleotide, which is intended to only bind to the template DNA, also binds to some degree to the secondary structure, causing cleavage of that structure. This cleavage creates a background signal that must be considered when determining the result of the assay. Consequently, invasion assays such as are represented by FIG. 2 have been run with a control, i.e., an assay in which template, or target, DNA is not present. The fluorescent signal measured at the completion of this control assay is the signal due to the undesired cleavage of the secondary structure by the primary invader oligonucleotide. This control signal is subtracted from that measured at the completion of the test assay (i.e., the assay with the template DNA) to provide an approximation of the signal due only to an overlap between the invader oligonucleotide and probe oligonucleotides in the primary invasion reaction. In theory, a positive net signal indicates that the invader oligonucleotide and probe oligonucleotide are complementary to different parts of the DNA template and overlap.

The invasion assay is a powerful analytical tool that can be used to supplement, or even replace, existing assays such as PCR. It is desirable, however, to increase its speed and accuracy. It is also desirable to reduce the amount of probe material that must be used to provide a useful (e.g., reliable) result. These and other needs are met by the invention disclosed herein.

SUMMARY OF THE INVENTION

This invention is directed to an improved invasion assay and to methods of analyzing invasion assay data. The invention is based, in part, on a discovery that signals due to the cleavage of a probe annealed to a template polynucleotide (e.g., DNA or RNA) can exhibit behavior over time that is different from the behavior over time of signals produced by background reactions (e.g., reactions that are not dependent on the presence of target polynucleotide). For example, the positive signal produced by many invasion assays (i.e., the signal that indicates an cleavage of a probe oligonucleotide annealed to a target polynucleotide) can be fit to a polynomial that is higher in order than the polynomial required to characterize background signal.

It is thus possible to determine the results of an invasion assay in real time or at the conclusion of the assay by determining whether the behavior of the signal it produced over time is different from that of a typical, estimated, theoretical or actually measured background signal.

BRIEF DESCRIPTION OF THE DRAWINGS

FIG. 2 provides a schematic representation of a type of invasion assay herein referred to as a "cascade invasion assay."

DEFINITIONS

Figure 1A:
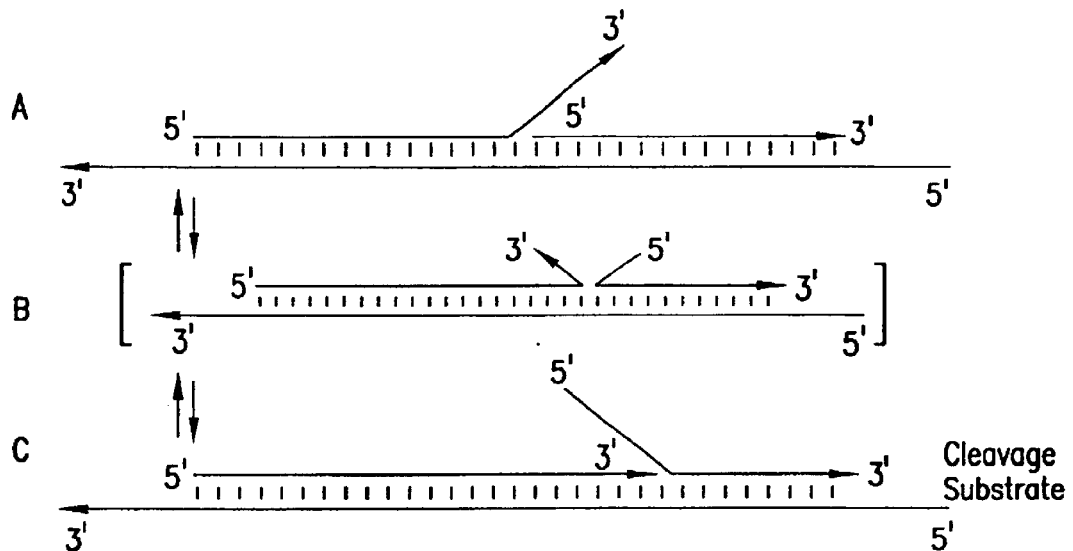
FIG. 1A provides a schematic representation of the configurations assumed by oligonucleotides with an overlap complementary to a DNA target. The 3' end of the upstream oligonucleotide (A) or the 5' end of the downstream oligonucleotide (C) can each be displaced by the other, with both conformers interchanging through an intermediate form (B). Endonucleases such as FEN1 cleave only the flap created by displacement of the downstream segment (C). See Lyamichev, V., et al., *Nature Biotech.* 17:292–296 (1999).
Figure 1B:
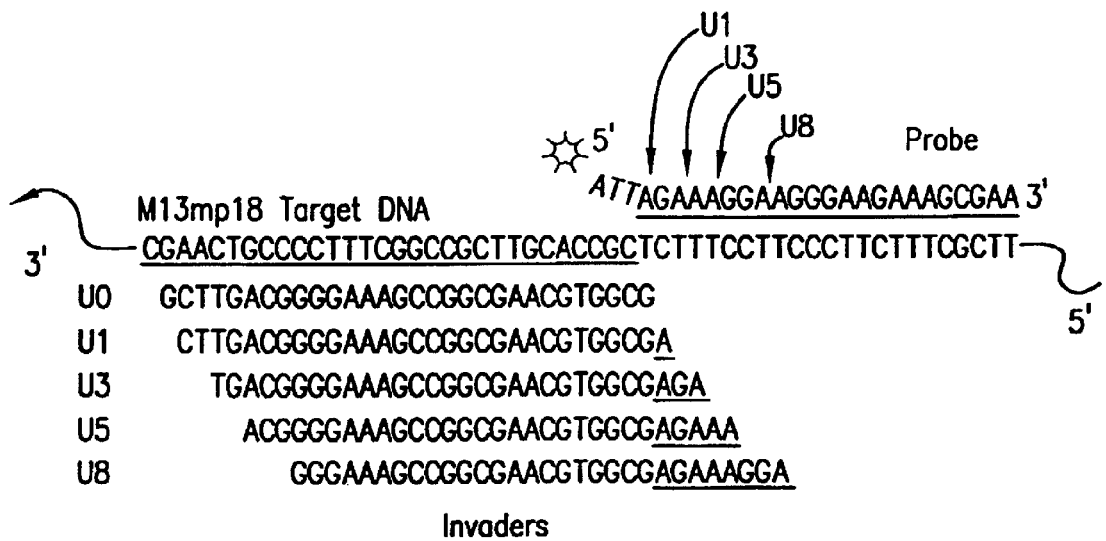
FIG. 1B provides an example of a target region and the cleavage structures resulting form the overlap of 0, 1, 3, 5, and 8 nucleotides and the structure of a probe and five invader oligonucleotides. (SEQ ID NOS. 1–7). The underlined nucleotides at the 3' end of the invader oligonucleotides indicate the extent of the overlap with the probe oligonucleotide. The labeled arrows above the probe show the cleavage points induced by each invader oligonucleotide. The star indicates a fluorescent label. See Lyamichev, V., et al., *Nature Biotech.* 17:292–296 (1999).

"Nucleobase:" refers to a substituted or unsubstituted nitrogen-containing parent heteroaromatic ring of a type that is commonly found in polynucleotides. Typically, but not necessarily, the nucleobase is capable of forming Watson-Crick and/or Hoogsteen hydrogen bonds with an appropriately complementary nucleobase. Exemplary nucleobases include, but are not limited to, purines such as 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG) hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. Additional exemplary nucleobases can be found in Fasman, 1989, *Practical Handbook of Biochemistry and Molecular Biology*, pp. 385–394, CRC Press, Boca Raton, Fla., and the references cited therein. Preferred nucleobases are purines, 7-deazapurines and pyrimidines. Particularly preferred nucleobases are the normal nucleobases, defined infra, and their common analogs, e.g., 2ms6iA, 6iA, 7-deaza-A,D, 2dmG, 7-deaza-G, 7mG, hypoxanthine, 4sT, 4sU and Y.

"Normal Nucleobase:" refers to a nucleobase that is naturally-occurring and encoding, i.e., adenine, cytosine, guanine, thymine or uracil.

"Nucleoside:" refers to a compound consisting of a nucleobase covalently linked, typically via a heteroaromatic ring nitrogen, to the C1' carbon of a pentose sugar. Typical pentose sugars include, but are not limited to, those pentoses in which one or more of the carbon atoms are each independently substituted with one or more of the same or different —R, —OR, —NRR or halogen groups, where each R is independently hydrogen, ($C_1$–$C_6$) alkyl or ($C_5$–$C_{14}$) aryl. The pentose sugar may be saturated or unsaturated. Exemplary pentose sugars include, but are not limited to, ribose, 2'-deoxyribose, 2'-($C_1$–$C_6$)alkoxyribose, 2'-($C_5$–$C_{14}$) aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$–$C_6$)alkylribose, 2'-deoxy-3'-($C_1$–$C_6$)alkoxyribose, 2'-deoxy-3'-($C_5$–$C_{14}$)aryloxyribose, 2',3'-dideoxy-3'-haloribose and 2',3'-dideoxy-3'-fluororibose.

When the nucleobase is a purine or a 7-deazapurine, the pentose sugar is attached to the N9 or C8 position of the nucleobase. When the nucleobase is a pyrimidine, the pentose sugar is attached to the N1-position of the nucleobase (see, e.g., Kornberg and Baker, 1992, *DNA Replication*, 2$^{nd}$ Ed., Freeman, San Francisco), except for pseudouridines, in which the pentose sugar is attached to the C5 position of the uracil nucleobase. Preferred nucleosides are those in which the nucleobase is a purine, a 7-deazapurine, a pyrimidine, a normal nucleobase or a common analog of a normal nucleobase and the pentose sugar is any of the exemplary pentose sugars listed above.

"Normal Nucleoside:" refers to a compound consisting of a normal nucleobase covalently linked via the N1 (C, T or U) or N9 (A or G) position of the nucleobase to the C1' carbon of ribose or 2'-deoxyribose.

"Nucleoside Analog:" refers to a nucleoside in which the pentose sugar is replaced with a pentose sugar analog. Exemplary pentose sugar analogs include, but are not limited to, substituted or unsubstituted furanoses having more or fewer than 5 ring atoms, e.g., erythroses and hexoses and substituted or unsubstituted 3–6 carbon acyclic sugars. One or more of the carbon atoms may be independently substituted with one or more of the same or different —R, —OR, —NRR or halogen groups, where each R is independently hydrogen, ($C_1$–$C_6$) alkyl or ($C_5$–$C_{14}$) aryl.

"Nucleotide:" refers to a nucleoside in which one or more, typically one, of the pentose carbons is substituted with a phosphate ester having the formula:

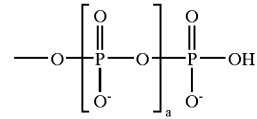

where α is an integer from 0 to 4. Preferably, α is 2 and the phosphate ester is attached to the 3'- or 5'-carbon of the pentose. Particularly preferred nucleotides are those in which the nucleobase is a purine, a 7-deazapurine, a pyrimidine, a normal nucleobase or a common analog thereof.

"Normal Nucleotide:" refers to a normal nucleoside in which the 3'- or 5'-carbon of the ribose or 2'-deoxyribose is substituted with a phosphate ester having the formula:

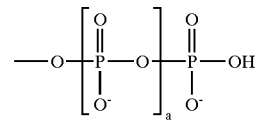

where α is an integer from 0 to 2. Preferred normal nucleotides are those in which α is 2 and the phosphate ester is attached to the 5'-carbon of the ribose (NTP) or 2'-deoxyribose (dNTP).

"Nucleotide Analog:" refers to a nucleotide in which the pentose sugar and/or one or more of the phosphate esters is replaced with its respective analog. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present.

Also included within the definition of "nucleotide analog" are nucleobase monomers which can be polymerized into polynucleotide analogs in which the DNA/RNA phosphate ester and/or sugar phosphate ester backbone is replaced with a different type of linkage.

"Nucleoside/tide:" refers to a nucleoside and/or a nucleotide and/or a mixture thereof.

"Polynucleotide:" refers to a linear polymeric chain of nucleoside monomer units that are covalently connected to one another by phosphate ester internucleoside linkages. Unless stated otherwise, "polynucleotide" as used herein includes polymers of any length, including oligonucleotides, polynucleotides and polynucleotides as those terms are commonly used in the art. Where polynucleotides of specific size ranges are intended, the number of monomer units is specifically delineated. Thus, polynucleotides according to the invention can range in size from a few monomer units (e.g., 4 to 40), to several hundreds of monomer units, to several thousands of monomer units, or even more monomer units. Whenever a polynucleotide is represented by a sequence of letters, e.g. "ATGCCTG," it will be understood that the sequence is presented in the 5'→3' direction. 2'-Deoxyribopolynucleotides are preceded with the letter "d," e.g. "d(ATGCCTG)."

Polynucleotides may be composed of a single type of sugar moiety, as in the case of RNA and DNA, or mixtures of different sugar moieties, as in the case of RNA/DNA chimeras.

DETAILED DESCRIPTION OF THE INVENTION

This invention is directed to an improved invasion assay that provides several advantages when compared to prior assays. These advantages include, but are not limited to, less probe necessary to provide a reliable result, less time required to provide a reliable result, the ability to determine or estimate assay results in real time (i.e., while data is being collected), and the ability to obtain reliable results without running control assays. The invention further encompasses a novel method of analyzing data provided by prior invasion assays. In each of the methods of the invention, data collection and/or analysis is preferably done by computer.

This invention is based on the discovery of time-dependent behavior of certain invasion assays, which are referred to herein as "cascade assays" or "cascade invasion assays." In cascade assays of this invention, such as those represented in FIG. 2, an invader oligonucleotide can hybridize to the target, or template, polynucleotide of interest (e.g., DNA or RNA). Invader oligonucleotides can be any oligonucleotide at least a portion of which can hybridize to the portion of the template that is of interest. Probes of the invention can hybridize with a region of the template that is contiguous and overlapping with the region to which the invader oligonucleotide can hybridize or otherwise associate. Invader oligonucleotides can contain regions that do not hybridize with the template, yet affect the cleavage of probe oligonucleotides. See, e.g., FIG. 5 of Harrington, J. J., and Lieber, M. R., *J. Biol. Chem.* 270(9):4503–4508, 4506 (1995), and the accompanying text.

Examples of invader oligonucleotides suitable for use in this invention include, but are not limited to, those identified as the "second oligonucleotide," "second oligo," or "invader" in U.S. Pat. No. 5,994,069 which is incorporated herein by reference. See, e.g., U.S. Pat. No. 5,994,069 at col. 37, lines 41–48. See also U.S. Pat. Nos. 5,843,669, 5,846, 717, 5,874,283, 5,888,780, 5,985,557, and 6,001,567, each of which is incorporated herein by reference; and International Patent Application Nos. WO 97/27214, WO 98/23774, and WO 98/42873, each of which is incorporated herein by reference. Examples of probes include, but are not limited to, those identified as the "first oligonucleotide," "first oligo," or "probe" in U.S. Pat. No. 5,994,069. See, e.g., U.S. Pat. No. 5,994,069 at col. 37, lines 37–41. See also U.S. Pat. Nos. 5,843,669, 5,846,717, 5,874,283, 5,888,780, 5,985,557, and 6,001,567; and International Patent Application Nos. WO 97/27214, WO 98/23774, and WO 98/42873.

The interaction between the invader oligonucleotide, probe oligonucleotide, and template, or target, polynucleotide in the assays of this invention is described, for example, in U.S. Pat. No. 5,994,069, International Patent Application No. WO 98/42873, and Harrington, J. J., and Lieber, M. R., *J. Biol. Chem.* 270(9):4503–4508 (1995), each of which is incorporated herein by reference. See, e.g., U.S. Pat. No. 5,994,069 at col. 37, line 30-col. 41, line 41; and FIG. 5 of Harrington, J. J., and Lieber, M. R., *J. Biol. Chem.* 270(9):4503–4508, 4506 (1995), and the accompanying text.

In a typical assay of the invention, if the invader oligonucleotide and probe oligonucleotide both anneal to the target substrate and overlap by at least one nucleotide, a cleavage structure is formed which comprises a flap of the probe. This flap can be cleaved by, for example, an endonuclease. Examples of endonucleases include, but are not limited to, those disclosed by U.S. Pat. Nos. 5,843,669, 5,846,717, 5,874,283, 5,888,780, 5,985,557, 5,994,069, and 6,001,567. Particularly preferred endonucleases are described, for example, by International Patent Application No. WO 98/23774. When cleaved, the flap can then anneal to another structure, forcing its cleavage and the production of yet another molecule. If desired, this process can continue a chain of reactions that will eventually provide a signal detected by the observer. Typically, however, the cleaved probe flap formed in the primary reaction induces the cleavage of what is referred to herein as a reporter precursor. Typically, the reporter precursor comprises reporter and quencher moieties, such as are shown in FIG. 2. Examples of reporter precursors are the hairpin structures disclosed, for example, by U.S. Pat. No. 5,994,069. See, e.g., U.S. Pat. No. 5,994,069 at col. 72, lines 11–67. See also U.S. Pat. Nos. 5,843,669, 5,846,717, 5,874,283, 5,888,780, 5,985,557, and 6,001,567; and International Patent Application Nos. WO 97/27214, WO 98/23774, and WO 98/42873. Cleavage of the reporter precursor provides a reporter that can be detected by conventional means such as, but not limited to, fluorescence.

It has now been discovered that the signal generated by a cascade (i.e., at least two) of cleavage reactions typically exhibits different behavior over time than a signal generated by different reactions or series of reactions. Reactions that provide a signal, but are not indicative of the cleavage process of interest (e.g., the primary reaction shown in FIG. 2), are referred to herein as background reactions. In typical cascade invasion assays of the invention, the background signal is linear in nature and can be fit to an equation of the formula:

$$S(t)=p_1+p_2t \qquad (1)$$

wherein t is time, $p_1$ is the signal at t=0, and $p_2$ is the rate of the signal increase. By contrast, the signal produced as a result of the primary reaction exhibits quadratic behavior, and is best fit to an equation of the formula:

$$S(t)=p_1+p_2t+p_3t^2 \qquad (2)$$

wherein $p_3$ is greater than zero. This difference in behavior is shown, for example, in FIG. 3.

Without being limited by theory, it is believed that the different time-dependent behavior of the background and target signals is due to the cleavage of multiple probes that can associate near or at their melting point with a single target or template to which a single primary invader oligonucleotide is also associated. The cleavage of each of these probes induces the cleavage of a reporter-quencher complex. Thus, over time, the overlap of a single primary invader oligonucleotide with multiple probes on a template can yield a large number of reporter fragments. By contrast, it is believed that the association of a single primary invader oligonucleotide with a reporter-quencher complex only produces one reporter fragment.

Whatever the actual cause of the difference in their time-dependent signals, it is now possible to differentiate between positive assay signals and background noise by simply observing the signal provided by an invasion assay as a function of time. For many cascade assays, this can be accomplished by simply fitting the data to Equation 2 and determining whether $p_3$ is greater than zero. As a practical matter, however, this approach has some limitations.

Theoretically, a linear growth curve is expected to produce a value of zero for the $t^2$ coefficient ($p_3$) when modeled using Equation 2. In practice, however, experimental noise makes it likely to have a non-zero value. It is therefore preferred that the assay conditions (e.g., the reagents used, the concentrations of the reactants, the specific invader oligonucleotides and probe oligonucleotides used, and the temperature) be adjusted to minimize background noise. However, another problem in assessing the significance of the $t^2$ coefficient is that the value of $p_3$ is highly influenced by factors such as, but are not limited to, reaction kinetics, acquisition time, and the concentrations of reactants. Consequently, the coefficient $p_3$ can assume any value in a large range of values. A preferred embodiment of the invention therefore limits the range of values that can be assumed by $p_3$. By doing so, the significance of $p_3$ can be assessed both empirically and theoretically in a realistic and predictable manner.

Although various ways in which this can be done will be apparent to those skilled in the art, one particular way in which this can be accomplished is by transformation. In this particular method, the independent variable, t, and the dependent variable, S(t), of Equation 2 are transformed to t* and S*(t*), respectively, such that their minima are each equal to zero and their maxima are each equal to unity. This transformation accomplishes two important goals. First, the transformation space (t*, S*(t*)) consists of three different regions: the linear growth functions fall within the first region, the quadratic growth functions in which $p_3$ is positive fall within the second region, and the quadratic growth functions in which $p_3$ is negative fall within the third region. Second, the value for $p_3$ associated with growth curves resulting from invasive cleavage is bounded.

Figure 4:
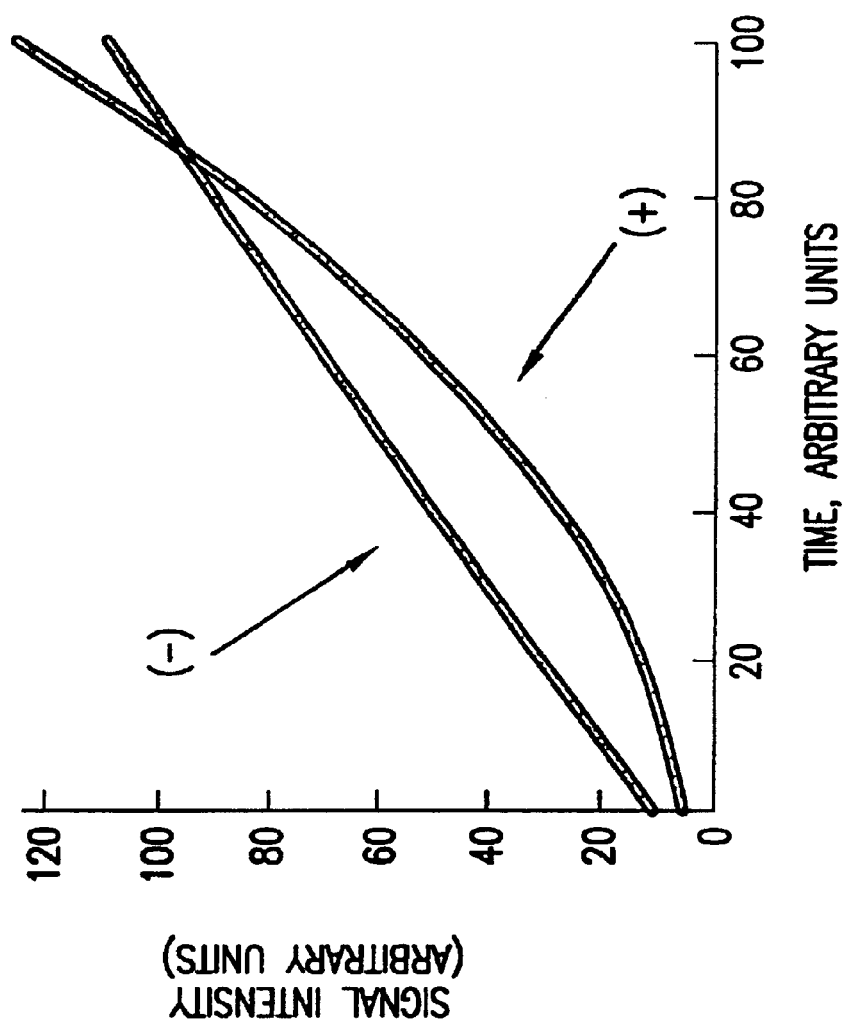
FIG. 4 shows idealized invasive cleavage assay response curves.
Figure 5A:
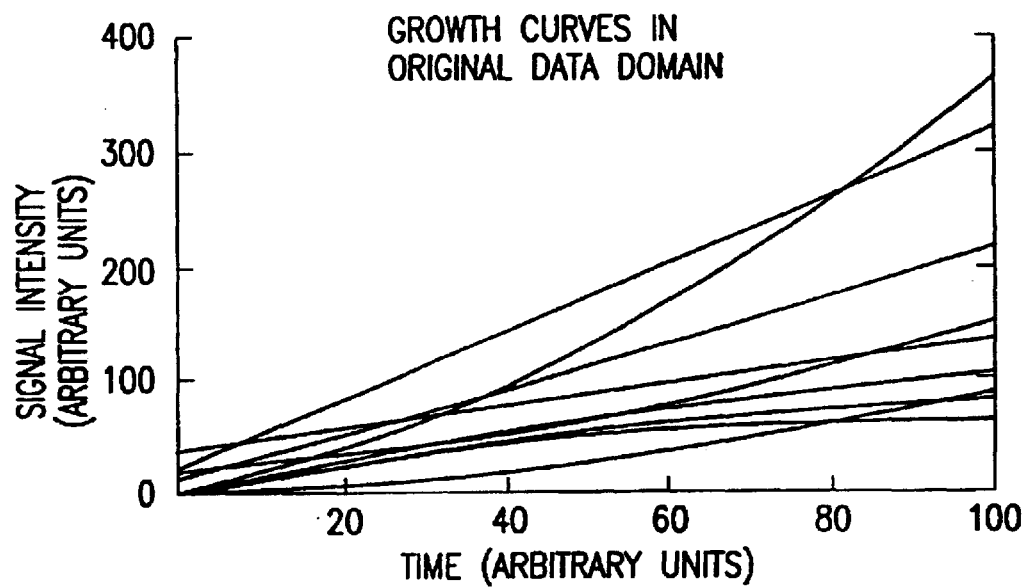
FIG. 5 shows the effect of domain transformation on a family of response functions simulated with added random noise.
Figure 5B:
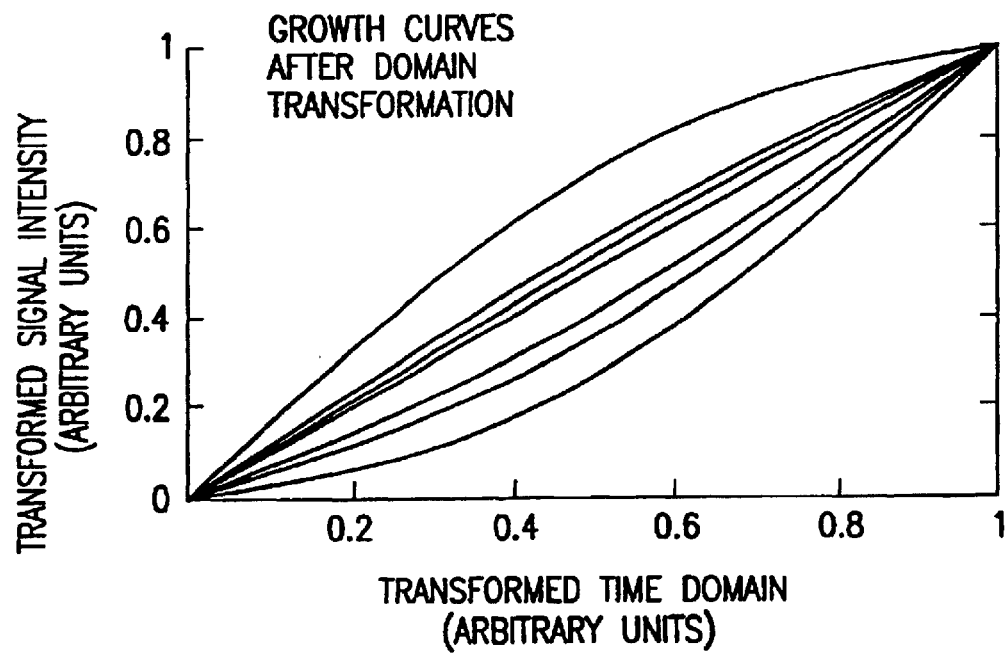

Under optimal conditions, the value of $p_3$ is less than or equal to unity (i.e., $p_3 \leq 1$). A threshold value for $p_3$ can thus be set independent of the conditions under which the invasive assay is run. FIG. 4 shows an idealized linear growth in signal due to background (negative) and an idealized quadratic growth in signal due to primary invasive cleavage (positive). FIG. 5 shows the effect of domain transformation on a family of response functions simulated with added random noise. To be specific, the top panel of FIG. 5 shows three different response functions (red), three different quadratic responses with positive curvature (green), and three different quadratic responses with negative curvature (yellow). As shown in the top panel, the response function can be in any region of the response space depending on factors such as, but not limited to, the concentration of the target, or template, molecule, and the nature of the background signal(s). By contrast, the transformation domain maps the three families of curves to distinct regions in the new domain. This is shown in the bottom panel of FIG. 5, wherein the three linear response functions are mapped to the same region and appear as one line, and the quadratic response functions appear on either side of that line depending on whether their curvature is positive or negative. The domain transformation of this invention thus achieves natural clustering of the response curves, which allows easy classification of the data obtained from the invasion assay. See Example 2, below.

Specific embodiments of the invention take into consideration the effects background (e.g., experimental) noise can have on the certainty of an analysis of assay data. For example, the negative region denoted by the red line in FIG. 5 is expected to have a finite width. The size of the permissible negative region is consequently determined in view of experimental and instrumental conditions, as well as the desired rate of false positive. For example, after the response function is transformed, the analytical signal can be modeled using linear and quadratic models and utilizing the least squares criteria, or any other criteria known to those skilled in the art. Referring to Equation 2, the $t^2$ term is then examined in view of the width of the negative region. The significance of the quadratic growth can then be estimated using the growth model attributed to background noise kinetics (e.g., linear growth), as a benchmark or absolute standard. In preferred embodiments of this invention, deviation from linearity is a measure of significance. This can be determined by, for example, the residuals of an assumed linear model.

A specific method of the invention can thus be described in terms of the following steps: (i) transformation of the growth curve data to new domain; (ii) the fitting of linear and quadratic models to the transformed growth curve data set; (iii) comparison of the $t^2$ term ($p_3$ in Equation 2) to the threshold values set to define the negative region; and (iv) if the growth curve is found to be in the positive region, the evaluation of the residuals obtained from the linear model fit for their significance. This specific embodiment of the invention is described in more detail in Example 2, below.

The improvements provided by this invention can be used with any variant of the invasion assay wherein the cleavage of one structure induces the cleavage of at least one additional structure. Examples of such assays include, but are not limited to, those disclosed by U.S. Pat. Nos. 5,843,669, 5,874,283, 5,888,780, 5,985,557, 5,994,069, and 6,001,567, each of which is incorporated herein by reference. In general, however, this invention can be applied to any assay wherein the desired signal exhibits different behavior as a function of time than that of the background signal(s). Instead of exhibiting quadratic behavior, for example, such a signal may exhibit behavior best represented by a higher order polynomial, such as is represented by Formula 3:

$$S(t)=\Sigma p_j t^k (j=1,2,\ldots;k=0,1,2,\ldots) \qquad (3)$$

Other mathematical relationships (e.g., exponential) may also best represent the signal of interest produced by a cascade assay. At the same time, the time-dependent background signal of an assay need not be linear: all that is necessary is a time-based behavior that can be determined and differentiated from that of the signal of interest.

In view of the breadth of the invention, and the fact that it can be applied to wide array of assays in addition to those currently known in the art, the following Examples are not to be construed as limiting the scope of the present invention.

EXAMPLES

Example 1

Data Accumulation and Simple Analysis

Advantages provided by this invention are apparent from the following experiment, which was performed using materials available from Applied Biosystems (Foster City, Calif.) and Third Wave Technologies (Madison, Wis.). An ABI PRISM 7700, available from Applied Biosystems, was used for data collection.

Using 100 ng human genomic DNA per test, the following reagents were used in the assay of this invention for detecting a C/T polymorphism in the human MFTHR gene: a "C" Probe Mix containing a flap-plus-probe oligonucleotide specific for the MTHFR C allele and the MTHFR-specific invader oligonucleotide; a "T" Probe Mix containing flap-plus-probe oligonucleotide specific for the MTHFR T allele and the MTHFR-specific invader oligonucleotide; a Signal Probe comprising fluorogenic oligonucleotide labeled with FAM reporter and CY3 quencher that is substrate for the secondary invasion reaction; a Signal Buffer which includes $Mg^{2+}$; and Cleavase-VIII™, which is a structure-dependent endonuclease that performs the cleavage reaction.

Human genomic DNA from 90 different individuals was analyzed in the experiment. The DNA from these individuals had previously been dried down in 7700 reaction plates, each well containing approximately 100 ng DNA. Each plate has 6 wells with no template. In one plate, 10 μl diluted "C" Probe Mix was added to each well. In a separate plate, 10 μl diluted "T" Probe Mix was added to each well. These plates were incubated at 95° C. for 5 minutes to denature the DNA, then placed on ice. The use of the ice incubation, which was not used in prior invasion assays, is designed to better preserve the single-stranded nature of the denatured DNA.

A reaction cocktail was made by mixing Signal Probe, Signal Buffer, Cleavase-VIII®, and ROX Passive Reference. Five microliters of this reaction cocktail was added to each well. After capping the wells, each plate was incubated at 65° C. for 90 minutes in the ABI PRISM 7700 with fluorescence data collected throughout. The fluorescence data were analyzed by using multicomponenting to determine the contributions of FAM, CY3, and ROX. For each well, the FAM signal was divided by the ROX signal and plotted versus incubation time.

Figure 3:
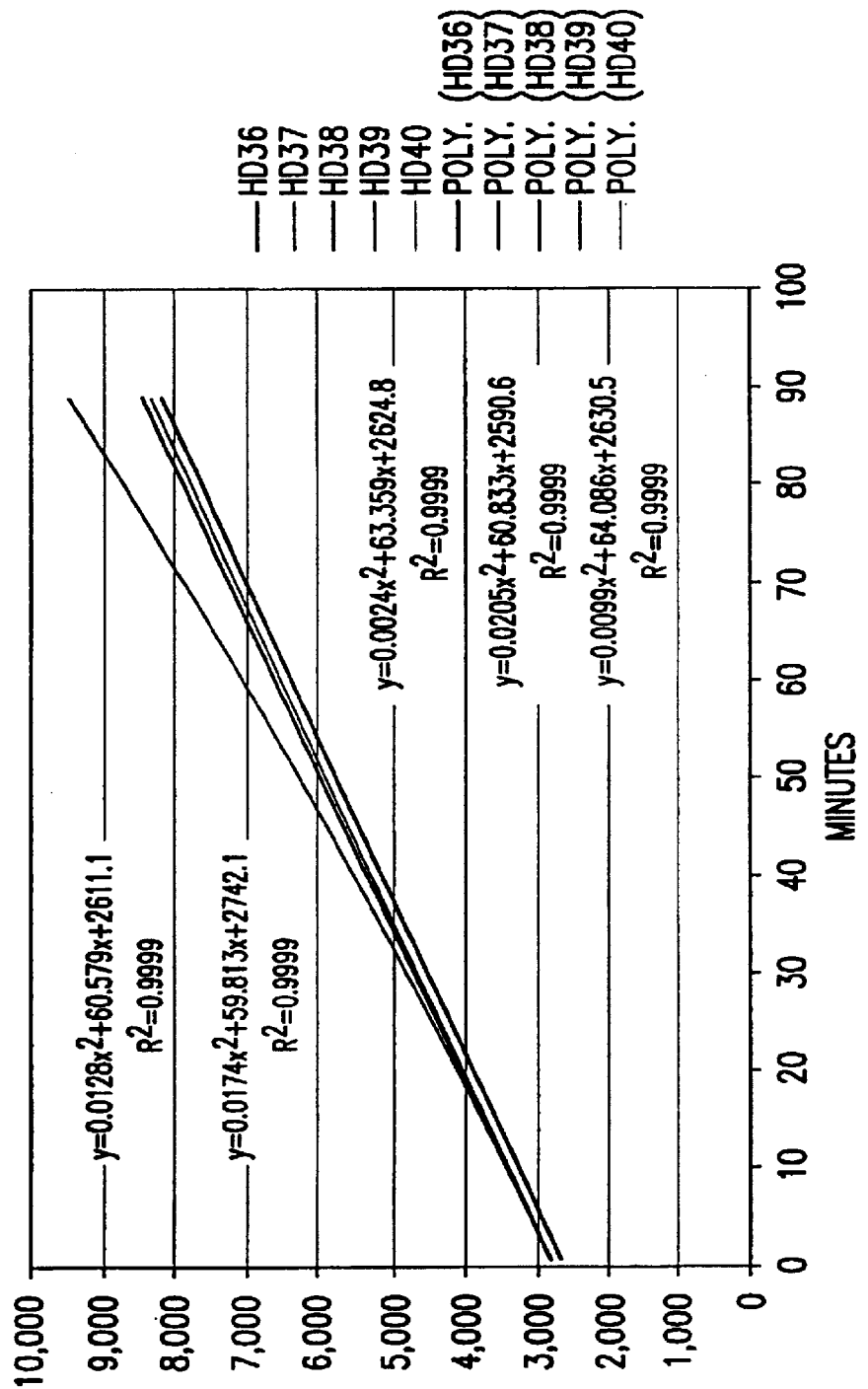
FIG. 3 shows one positive assay and four negative assays.
Figure 6B:
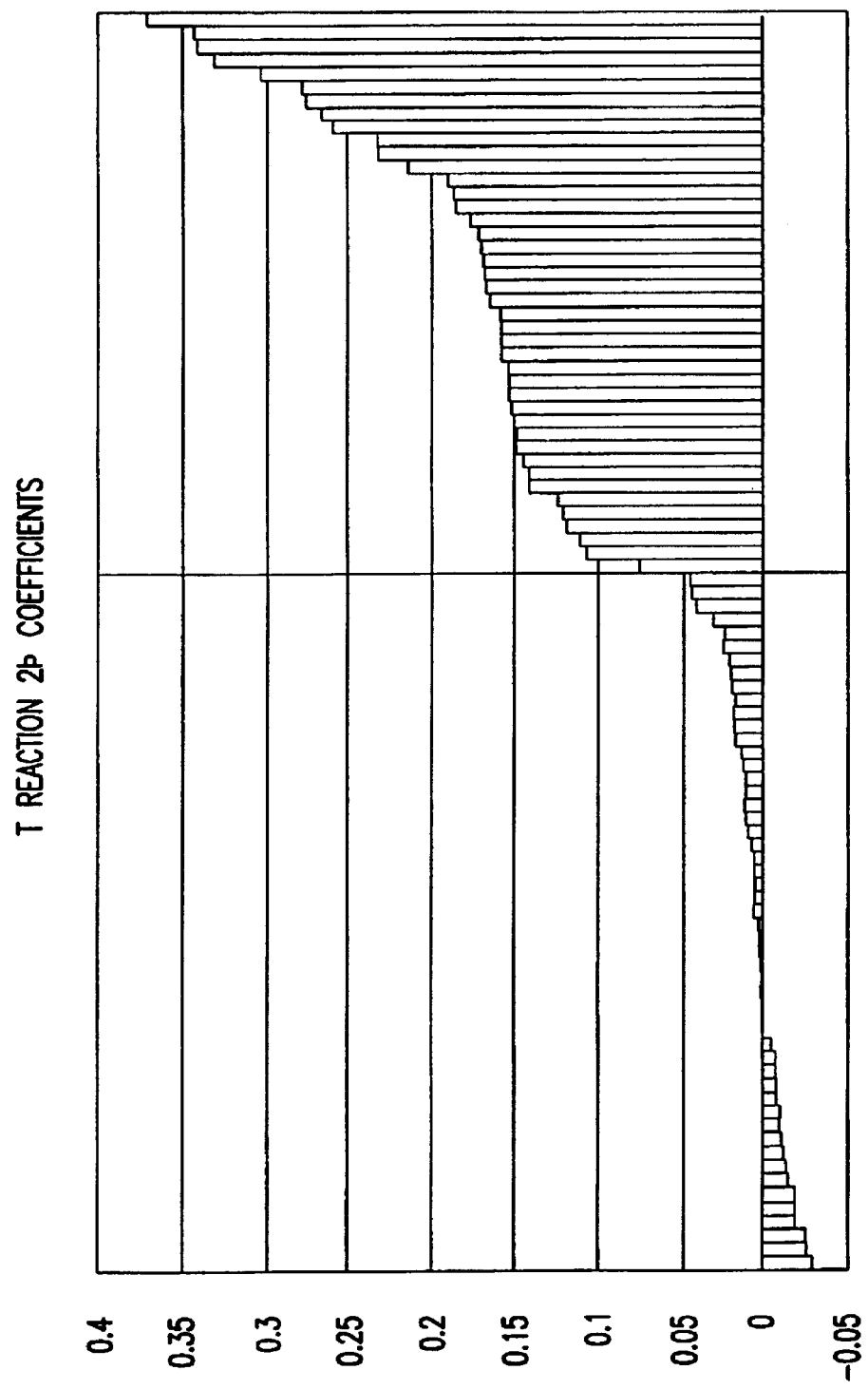
FIG. 6 shows the second order coefficients obtained from fits of the data shown in FIG. 3.

FIG. 3 shows the results for five wells from the "T" reaction plate. This plot shows the results from four negative samples and one positive sample (the curved trace). The negative samples show a linear increase in normalized FAM signal. This indicates there is background cleavage of the signal probe in the absence of the appropriate template. The same linear increase is signal is observed in No Template Control reactions. For the positive sample, the rate of FAM signal increase is accelerated relative to the linear increase seen in the negative samples. In fact, the increase in FAM signal observed in positive reactions is fit very well by a quadratic equation. Thus, positive and negative reactions can be distinguished by the second order term in the quadratic fit. A significant second order term indicates a positive reaction, whereas a second order term close to zero indicates a negative reaction. This is made clear by FIG. 6, which shows the second order coefficients from all the reactions, ranked from lowest to highest. In each plot, the vertical line running from the bottom to the top of the chart shows the separation of positive and negative samples. The student t-test indicates a 99.5% confidence for the separation in each case. Based on these separation lines, the genotype of each individual can thus be determined from the second order coefficients, as shown in Table 1.

TABLE 1

| Well | Sample | C 2 | T 2 | C Call | T Call | TaqMan Calls |
|---|---|---|---|---|---|---|
| 1 | HD6 | 0.2815 | 0.0079 | C | — | 1 |
| 2 | HD7 | 0.2761 | 0.0253 | C | — | 1 |
| 3 | HD8 | 0.1804 | 0.232 | C | T | 1 and 2 |
| 4 | HD9 | 0.1618 | 0.186 | C | T | 1 and 2 |
| 5 | HD10 | 0.0325 | 0.2328 | — | T | 2 |
| 6 | HD1 | 0.0302 | 0.3314 | — | T | 2 |
| 7 | HD2 | 0.2613 | 0.0129 | C | — | 1 |
| 8 | HD3 | 0.1657 | 0.1479 | C | T | 1 and 2 |
| 9 | HD4 | 0.2411 | 0.0053 | C | — | 1 |
| 10 | HD5 | 0.2506 | 0.0076 | C | — | 1 |
| 11 | HD16 | 0.098 | 0.1477 | C | T | 1 and 2 |
| 12 | HD17 | 0.1011 | 0.1076 | C | T | 1 and 2 |
| 13 | HD18 | 0.1111 | 0.1576 | C | T | 1 and 2 |
| 14 | HD19 | 0.1171 | 0.1417 | C | T | 1 and 2 |
| 15 | HD20 | 0.2619 | 0.0044 | C | — | 1 |
| 16 | HD11 | 0.0948 | 0.1116 | C | T | 1 and 2 |
| 17 | HD12 | 0.2566 | −0.0058 | C | — | 1 |
| 18 | HD13 | 0.138 | 0.1667 | C | T | 1 and 2 |
| 19 | HD14 | 0.4287 | −0.0171 | C | — | 1 |
| 20 | HD15 | 0.2535 | 0.0206 | C | — | 1 |
| 21 | HD26 | 0.1833 | 0.0131 | C | — | 1 |
| 22 | HD27 | 0.1328 | 0.1581 | C | T | 1 and 2 |
| 23 | HD28 | 0.131 | 0.1581 | C | T | 1 and 2 |
| 24 | HD29 | 0.4142 | 0.007 | C | — | 1 |
| 25 | HD30 | 0.1781 | 0.1863 | C | T | 1 and 2 |
| 26 | HD21 | 0.1129 | 0.1542 | C | T | 1 and 2 |
| 27 | HD22 | 0.2428 | 0.0424 | C | — | 1 |
| 28 | HD23 | 0.4112 | 0.0189 | C | — | 1 |
| 29 | HD24 | 0.1881 | 0.0081 | C | — | 1 |
| 30 | HD25 | 0.2729 | 0.0054 | C | — | 1 |
| 31 | HD36 | 0.2336 | 0.0128 | C | — | 1 |
| 32 | HD37 | 0.13 | 0.1704 | C | T | 1 and 2 |
| 33 | HD38 | 0.3513 | 0.0024 | C | — | 1 |
| 34 | HD39 | 0.3102 | 0.0205 | C | — | 1 |
| 35 | HD40 | 0.2399 | 0.0099 | C | — | 1 |
| 36 | HD31 | 0.312 | 0.0048 | C | — | 1 |
| 37 | HD32 | 0.0058 | 0.2662 | — | T | 2 |
| 38 | HD33 | 0.1126 | 0.1529 | C | T | 1 and 2 |
| 39 | HD34 | 0.2961 | 0.0075 | C | — | 1 |
| 40 | HD35 | 0.2629 | −0.024 | C | — | 1 |
| 41 | HD46 | 0.1723 | 0.1201 | C | T | 1 |
| 42 | HD47 | 0.1907 | 0.2137 | C | T | 1 and 2 |
| 43 | HD48 | 0.0329 | 0.2789 | — | T | 2 |
| 44 | HD49 | 0.2964 | 0.002 | C | — | 1 |
| 45 | HD50 | 0.2293 | −0.0037 | C | — | 1 |
| 46 | HD41 | 0.2028 | −0.0008 | C | — | 1 |
| 47 | HD42 | 0.2687 | 0.0113 | C | — | 1 |
| 48 | HD43 | 0.1778 | 0.1912 | C | T | 1 and 2 |
| 49 | HD44 | 0.2779 | −0.0269 | C | — | 1 |
| 50 | HD45 | 0.0721 | 0.0758 | C | T | 1 and 2 |
| 51 | HD56 | 0.3373 | −0.0126 | C | — | 1 |
| 52 | HD57 | 0.0998 | 0.125 | C | T | 1 and 2 |
| 53 | HD58 | 0.2663 | −0.0176 | C | — | 1 |
| 54 | HD59 | 0.3083 | 0.0443 | C | — | 1 |
| 55 | HD60 | 0.2629 | 0.0456 | C | — | 1 |
| 56 | HD51 | 0.3056 | −0.0055 | C | — | 1 |
| 57 | HD52 | 0.1653 | 0.1533 | C | T | 1 and 2 |
| 58 | HD53 | 0.0009 | 0.3418 | — | T | 2 |
| 59 | HD54 | 0.1921 | −0.0171 | C | — | 1 |
| 60 | HD55 | 0.1435 | 0.1495 | C | T | 1 and 2 |
| 61 | HD66 | 0.2506 | −0.0129 | C | — | 1 |
| 62 | HD67 | −0.0194 | 0.1696 | — | T | 2 |
| 63 | HD68 | 0.1384 | 0.1657 | C | T | 1 and 2 |
| 64 | HD69 | 0.1505 | 0.1715 | C | T | 1 and 2 |
| 65 | HD70 | 0.1394 | −0.0012 | C | — | 1 |
| 66 | HD61 | −0.0176 | 0.3705 | — | T | 2 |
| 67 | HD62 | −0.0221 | 0.1597 | — | T | 2 |
| 68 | HD63 | −0.0236 | 0.2764 | — | T | 2 |

TABLE 1-continued

| Well | Sample | C 2 | T 2 | C Call | T Call | TaqMan Calls |
|---|---|---|---|---|---|---|
| 69 | HD64 | 0.1469 | 0.0151 | C | — | 1 |
| 70 | HD65 | -0.017 | 0.3438 | — | T | 2 |
| 71 | HD76 | 0.0792 | 0.1218 | C | T | 1 and 2 |
| 72 | HD77 | 0.0932 | 0.005 | C | — | 1 |
| 73 | HD78 | 0.119 | 0.1414 | C | T | 1 and 2 |
| 74 | HD79 | 0.3541 | 0.0074 | C | — | 1 |
| 75 | HD80 | 0.2494 | 0.019 | C | — | 1 |
| 76 | HD71 | 0.2754 | 0.0234 | C | — | 1 |
| 77 | HD72 | 0.0859 | 0.1512 | C | T | 1 and 2 |
| 78 | HD73 | 0.0933 | 0.1453 | C | T | 1 and 2 |
| 79 | HD74 | 0.2836 | 0.0241 | C | — | 1 |
| 80 | HD75 | 0.234 | -0.0084 | C | — | 1 |

In Table 1, the column marked "TaqMan Calls" reports the genotypes previously determined for these individuals using a TaqMan™ assay. As used in the table, "1" means C homozygote; "2" means T homozygote; and "1 and 2" means C/T heterozygote. The red circle shows the only discrepancy between the INVADER™ and TaqMan™ data.

Example 2

Alternative Data Analysis

Comparison of the coefficients determined from a fit of the data obtained in Example 1 can be used to evaluate the results of assay. This simple method can provide erroneous results, however, since even small quadratic coefficients can indicate a positive signal, while relatively large ones may simply be artifacts of the fitting process. Therefore, it is preferred that analysis of the data, whether performed at the conclusion of the experiment or in real time, focus instead on the shape of the function to which the data is fit, rather than the coefficients calculated by simply fitting the data to a quadratic equation.

Figure 7A:
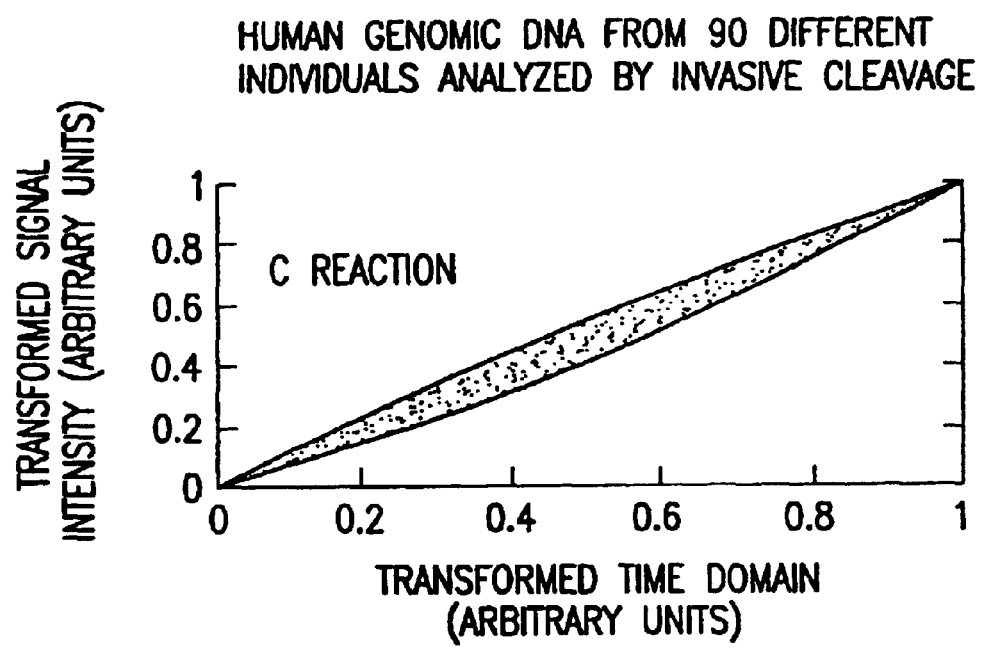
FIG. 7 shows the transformation of experimental responses obtained from the data shown in FIG. 3.
Figure 7B:
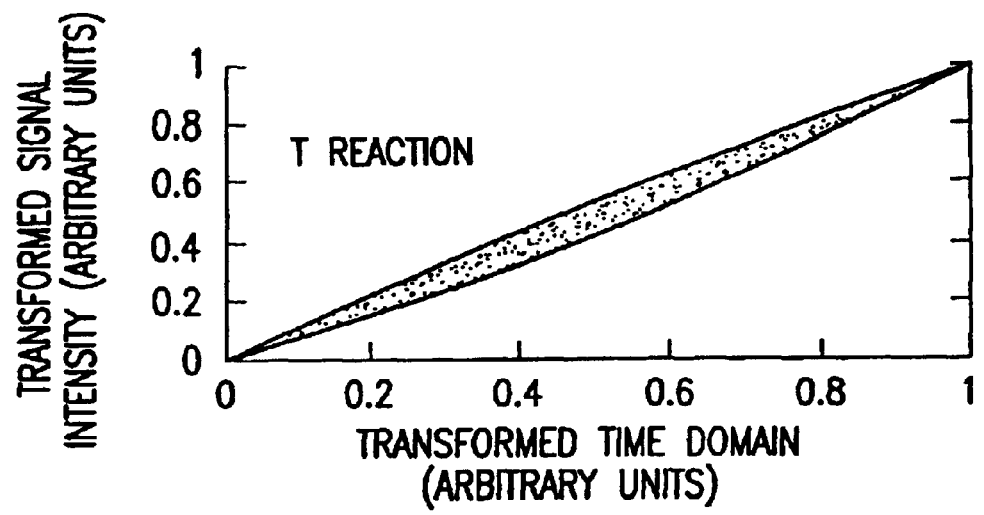

Using the transformation method described herein, transformed response functions were generated from the data obtained in Example 1. FIG. 7 shows these transformed response functions. The statistical significance of these results were then determined.

Using transformed signals from wells 5 and 19 of the data described in Example 1, residuals from fitting a linear growth model to the negative (well 5) and positive (well 19) profiles were obtained. In the case of well 5, where the signal growth is linear, the residuals exhibit the expected behavior; they are distributed about zero and cross the "zero line" very frequently. By contrast, the residuals from well 19, where the signal growth is quadratic, cluster on the positive side of zero and the negative side of zero, and do not cross the zero line as frequently. The larger the deviation from linearity, the fewer the number of crossing. Thus, the number of zero crossings in a population of residuals obtained after fitting a linear model to a time-varying profile, in this case the transformed signal vs. the transformed time, is an indicator of how significantly the profile deviates from a straight line. See, e.g., S. Siegel, "Nonparametric Statistics," McGraw-Hill, New York, 1956, p52; and N. Draper and H. Smith, "Applied Regression Analysis," Third Edition, John Wiley & Sons, Inc., New York, 1998, p1 92.

The number of crossings was examined in terms of the number of runs in the residuals. A run may be defined as a succession of residuals with the same sign which are preceded and followed by residuals of a different sign or by no residuals. See S. Siegel, "Nonparametric Statistics," McGraw-Hill, New York, 1956, p52. For example the following set of 10 residuals consisting of {+0.5, +0.1, -0.2, -0.4, -0.5, -0.6, -0.3, -0.2, -0.1, and +0.2} said to contain 3 runs. The number of runs in any given population of residuals is an indication of whether or not the residuals are randomly distributed. For a large (e.g., greater than about 20) sample of residuals where there are n positive residuals, m negative residuals, and r runs, the significance is estimated from the expected distribution of r whose mean, $\mu_r$, and standard deviation, $\sigma_r$, are given as:

$$\mu_r = 1 + (2\ nm)/(n+m) \quad (4)$$

$$\sigma_r = (A/B)^{1/2} \quad (5)$$

where $A = 2\ nm(2\ nm - n - m)$ and $B = (n+m)^2(n+m-1)$. A normalized r value, $r^*$, is calculated according to:

$$r^* = (r - \mu_r)/\sigma_r \quad (6)$$

Equation (6) expresses the number of runs, r, in terms of its deviation from expected value, given the sample size, n and m, in units of standard deviations. The significance of such deviation is consequently assessed under the null hypothesis that n and m occur in random order. The null hypothesis is rejected when $r^*$ cannot be accounted for by random arrangement at a given level of significance. In such cases the residuals are deemed systematic and the linear model invalid, i.e., the growth curve is non-linear at the desired level of significance.

The $r^*$ values estimated by Equation (6) for wells 5 and 19 were obtained. In the case of well 5, the normalized number of runs is within half a standard deviation unit from the expected mean; the linear model is, therefore, accepted. In the case of well 19, the normalized number of runs is more than 23 standard deviation units from the expected mean and the linear model is rejected. While many statistical models may be used, Tchebycheff's model provides a robust, and conservative, approach. See, e.g., R. Kirk, "Introductory Statistics," Wadsworth Publishing Company, Inc., Belmont, Calif, 1978, p83. Tchebycheff's theorem can be summarized as shown in equation (7):

$$P\{|x-\mu| \geq k\sigma\} < 1/k^2 \quad (7)$$

According to equation (7), the probability that a random variable is greater than k units of standard deviation away from its mean is less than $1/k^2$. Consequently, the larger the absolute value of $r^*$ in equation (6), the higher the probability that the residuals are not randomly distributed about zero and the linear model is rejected at the $(1-(1/k^2))$ significance level (also referred to as "confidence level").

The statistical significance test summarized above provides important feedback to the users vis-à-vis the selected threshold for $p_3$ and the width of the 'negative region." As mentioned above, growth curves with $p_3$ values that exceed a threshold value are tested for significance. When the threshold is set too low, the results classified as positives, because the $t^2$ terms exceeds the threshold value, are expected to have a high number of runs, and, thus, low significance level (k in Equation (7)). Users can therefore use the significance level as a guide in setting the limits of the "negative region."

The distribution of runs in the residuals enables users to obtain robust and sensitive statistical confidence estimates. Because the linear model provides an "absolute" standard, unbiased estimation of detection and classification confidence/significance can be derived from a single sample.

The embodiments of the invention described above are intended to be merely exemplary, and those skilled in the art will recognize, or will be able to ascertain using no more than routine experimentation, numerous equivalents of the specific materials, procedures, and devices described herein. All such equivalents are considered to be within the scope of the invention and are encompassed by the appended claims.

We claim:

1. A method of detecting a target polynucleotide which comprises the steps of:
   (a) contacting a target polynucleotide having a first portion and a second portion immediately contiguous to one another with:
      (i) an invader oligonucleotide, at least a part of which is capable of specifically hybridizing to the first portion of the target polynucleotide;
      (ii) a probe oligonucleotide comprising a first region that is capable of specifically hybridizing to the second portion of the target polynucleotide and a flap region located adjacent to the first region; and
      (iii) a reagent that is capable of cleaving the flap region of the probe oligonucleotide when the probe oligonucleotide is hybridized to the second portion of the target polynucleotide and the invader oligonucleotide is hybridized to the first portion of the polynucleotide;
   under conditions such that the cleaved flap region of the probe oligonucleotide and the reagent can come into contact with a reporter precursor to which the flap region of the probe oligonucleotide is capable of hybridizing to form a complex that can be cleaved by the reagent to provide a reporter capable of being detected;
   (b) obtaining a data set $(t, S(t))$, wherein t is time and $S(t)$ is signal as a function of time, by detecting the reporter at a plurality of times; and
   (c) transforming $(t, S(t))$ to provide a transformed data set $(t^*, S^*(t^*))$ wherein $t^*$ and $S^*(t^*)$ have minima of zero and maxima of unity, and determining whether the transformed data set exhibits non-linear behavior;
   wherein the target polynucleotide is detected if the transformed data set exhibits non-linear behavior.

2. The method of claim 1 wherein the invader oligonucleotide comprises a first region that is capable of specifically hybridizing to the first portion of the target polynucleotide, and a flap region located adjacent to the first region.

3. The method of claim 2 wherein the flap region of the invader oligonucleotide is capable of specifically hybridizing to the target polynucleotide.

4. The method of claim 2 wherein flap region of the invader oligonucleotide is not capable of specifically hybridizing to the target polynucleotide.

5. The method of claim 2 wherein flap region of the invader oligonucleotide comprises a first section that is not capable of specifically hybridizing to the target polynucleotide, and a second section that is capable of specifically hybridizing to the target polynucleotide.

6. The method of claim 1 wherein the second portion of the target polynucleotide is located immediately 3' to the first portion of the target polynucleotide.

7. The method of one of claims 2–5 wherein the flap region of the invader oligonucleotide is located immediately 3' to the first region of the invader oligonucleotide, and the flap region of the probe is located immediately 5' to the first region of the probe.

8. The method of claim 1 wherein the signal is fluorescence or phosphorescence.

9. The method of claim 1 wherein the determination of whether the signal exhibits a specific behavior as a function of time is performed in real time.

10. The method of claim 1 wherein the non-linear behavior is quadratic.

11. A method of detecting a target polynucleotide which comprises the steps of:
   (a) contacting a target polynucleotide having a first portion and a second portion immediately contiguous to one another with:
      (i) an invader oligonucleotide, at least a part of which is capable of specifically hybridizing to the first portion of the target polynucleotide;
      (ii) a probe oligonucleotide comprising a first region that is capable of specifically hybridizing to the second portion of the target polynucleotide and a flap region located adjacent to the first region; and
      (iii) a reagent that is capable of cleaving the flap region of the probe oligonucleotide when the probe oligonucleotide is hybridized to the second portion of the target polynucleotide and the invader oligonucleotide is hybridized to the first portion of the polynucleotide;
   under conditions such that the cleaved flap region of the probe oligonucleotide and the reagent can come into contact with a reporter precursor to which the flap region of the probe oligonucleotide is capable of hybridizing to form a complex that can be cleaved by the reagent to provide a reporter capable of being detected;
   (b) obtaining a data set $(t, S(t))$, wherein t is time and $S(t)$ is signal as a function of time, by detecting the reporter at a plurality of times; and
   (c) fitting $(t, S(t))$ to a quadratic function, transforming the quadratic function to yield a transformed function having independent and dependent variables having minima of zero and maxima of unity, and determining whether the transformed function exhibits non-linear behavior;
   wherein the target polynucleotide is detected if the transformed function exhibits non-linear behavior.

12. The method of claim 11 wherein the non-linear behavior is quadratic.

* * * * *